(12) United States Patent
Moscatello

(10) Patent No.: US 9,487,755 B2
(45) Date of Patent: *Nov. 8, 2016

(54) CELL CULTURE MEDIA, KITS AND METHODS OF USE

(76) Inventor: David Moscatello, Philadelphia, PA (US)

( * ) Notice: Subject to any disclaimer, the term of this patent is extended or adjusted under 35 U.S.C. 154(b) by 620 days.

This patent is subject to a terminal disclaimer.

(21) Appl. No.: 13/194,900

(22) Filed: Jul. 29, 2011

(65) Prior Publication Data

US 2013/0029414 A1    Jan. 31, 2013
US 2016/0298079 A9    Oct. 13, 2016

Related U.S. Application Data

(63) Continuation-in-part of application No. 11/542,863, filed on Oct. 4, 2006, now Pat. No. 7,989,205.

(60) Provisional application No. 60/723,804, filed on Oct. 6, 2005.

(51) Int. Cl.
*C12N 5/00* (2006.01)
*C12N 5/0775* (2010.01)

(52) U.S. Cl.
CPC ........ *C12N 5/0663* (2013.01); *C12N 5/0667* (2013.01); *C12N 2500/25* (2013.01); *C12N 2500/32* (2013.01); *C12N 2500/36* (2013.01); *C12N 2500/38* (2013.01); *C12N 2500/40* (2013.01); *C12N 2500/42* (2013.01); *C12N 2500/44* (2013.01); *C12N 2500/46* (2013.01); *C12N 2501/11* (2013.01); *C12N 2501/135* (2013.01)

(58) Field of Classification Search
None
See application file for complete search history.

(56) References Cited

U.S. PATENT DOCUMENTS

| 7,989,205 B2 * | 8/2011 | Moscatello | 435/407 |
| 2004/0132183 A1 * | 7/2004 | Scharp et al. | 435/366 |
| 2007/0082394 A1 * | 4/2007 | Moscatello | 435/325 |

FOREIGN PATENT DOCUMENTS

KR    2006021771 A  *  3/2006

OTHER PUBLICATIONS

Wesierska-Gadek, J et al "Phenol Red in the Culture Medium Strongly Affects the Susceptibility of Human MCF-7 Cells to Roscovitine" Cell Mol. Biol. Lett., Jan. 19, 2007, 12(2), pp. 280-293.*
Berthois, Y; Katzenellenbogen, JA; Katzenellenbogen, BS "Phenol Red in Tissue Culture Media is a Weak Estrogen: Implications Concerning the Study of Estrogen-responsive Cells in Culture" PNAS, Apr. 1986, 83, 2496-2500.*
Schindel, F; Andersen, C; Bosse, D "Comparision of Recombinant Human Albumin with Human Serum Albumin: Safety, Tolerability and Pharmacodynamics" J. Clin. Pharmacol.: 32nd Ann. ACCP Mtg.(abstract 76), 2003,43, pp. 1032-1033.*

* cited by examiner

*Primary Examiner* — Louise W Humphrey
*Assistant Examiner* — Aaron J Kosar

(57) ABSTRACT

Albumin-supplemented and xenogeneic product-free cell culture media, cell culture media supplements, and cell culture media kits for the support of primary culture of normal non-hematopoietic cells of mesodermal origin suitable for both research and clinical applications.

1 Claim, 8 Drawing Sheets

CELL CULTURE MEDIA, KITS AND METHODS OF USE

CROSS REFERENCE TO RELATED APPLICATION

The present application is a continuation-in-part and claims the benefit of U.S. patent application Ser. No. 11/542,863 filed Oct. 4, 2006 issued as U.S. Pat. No. 7,989,205, which claims the benefit of U.S. Provisional Patent Application No. 60/723,804, filed Oct. 6, 2005, both of which are incorporated herein by reference in their entirety.

FIELD OF THE INVENTION

The present invention relates to in general to cell culture media, cell culture media kits and methods for their use. More particularly, the invention provides cell culture media, kits and methods for their use in both research and clinical applications.

BACKGROUND OF THE INVENTION

Basal culture media used to grow human and non-human animal cells in the laboratory are typically composed of inorganic salts, buffers, glucose, amino acids and vitamins. These media are generally supplemented with animal-derived additives, most commonly fetal bovine serum (FBS), but also human serum, or other animal sera, and sometimes with extracts from other tissues. Additionally, other xenogeneic (from a species different than the cells being grown) factors are sometimes utilized to promote the growth and attachment of cells from human or non-human animal tissues. These xenogeneic supplements provide growth factors, hormones, lipids, trace elements, adhesion molecules, and uncharacterized factors, which may act alone or in concert to promote, inter alia, cell survival, cell adhesion, and cellular proliferation.

However, the use of xenogeneic animal-derived additives in cell cultures poses a number of problems for the subsequent therapeutic or clinical use of cells grown in such media. These problems include the risk of transmission of infectious agents such as mycoplasma, viruses and prions (e.g., bovine spongiform encephalopathy). Such infectious agents could pose a health risk to patients treated with cells or cell products grown in the presence of xenogeneic supplements. In addition, cells exposed to xenogeneic proteins will internalize the proteins, which can subsequently be processed and presented on the cell surface, which could result in an immune response against the cells resulting in their destruction and therapeutic failure.

Furthermore, even exposure of cells cultivated for therapeutic use to uncontaminated animal-derived supplements (e.g., sera or plasma) can be detrimental to the growth, viability, or desired behavior of cell cultures. More specifically, in the human clinical context, the serum or plasma must be matched to blood type (e.g., type A serum or plasma must be used to culture cells for use with a person with blood type A). This matching of blood type is necessary because of the presence of antibodies to the antigen not present on the donor blood cells. By way of example, plasma or serum from a blood type A person has antibodies to the blood type B antigen, and vice versa. Moreover, the present inventor is aware only of human serum being used to cultivate human cells, primarily white blood cells, in the laboratory environment. Because of its relatively high procurement cost versus its presently limited cell culture applications, human serum is prohibitively expensive for routine laboratory use.

In addition, different batches of serum, whether human or other animal, differ in their precise compositions. These variations may include but are not limited to the nature of the antibodies and hormones present in the batches which can significantly affect the behavior of cells grown in serum-containing media. For instance, for even routine laboratory cell culture use, a new lot of fetal bovine serum must be tested against old lots before purchasing the new lot in order to determine the extent of variance between the lots.

Species-matched albumin has been proposed as a basal culture medium supplement in lieu of serum or plasma. However, it is believed that albumin has been used exclusively for the cultivation of hematopoietic (or blood-forming) cells. The present inventor is aware of no prior implementations of species-matched albumin as a basal culture medium supplement for cultivation of non-hematopoietic cells suitable for therapeutic and research applications.

Thus, a need exists for a serum-free and xenogeneic product-free cell culture medium for the development of low-risk cell cultures or engineered tissues for human or veterinary therapeutic use.

A further need exists for a xenogeneic product-free cell culture medium for the development of low-risk cell cultures or engineered tissues for human or veterinary research use.

A further need exists for a cell culture medium comprising a basal medium and a supplement including a species-matched albumin for the cultivation of non-hematopoietic animal cells.

SUMMARY OF THE INVENTION

The present invention provides cell culture media, kits and methods of primary culture of normal mesenchymal stem cells, adipose stromal cells and other mesodermal tissue-derived stem and progenitor cells for both research and clinical applications. As used herein, the term "primary culture" means the cultivation of new rather than pre-established or immortalized cell lines. Further, as used herein, the term "normal" refers to healthy, normally functioning cells as opposed to mutant, malignant or otherwise abnormal cells. Additionally, as used herein, the term "research" means uses of cell culture media to cultivate cells exclusively for laboratory study purposes. That is to say, research-grade cultured cells are not introduced into a human or other animal subject upon cultivation. In contrast, the terms "clinical" or "therapeutic" mean uses of cell culture media to cultivate cells for reimplantation or transplantation into a human or other animal subject. In both research and clinical/therapeutic implementations, the media and methods according to the invention utilize albumin-supplemented and xenogeneic product-free cell culture media. In all instances, whether research or clinical, the albumin supplement selected for use in a particular medium is of the same species of origin as the cells to be cultivated (i.e., human albumin is used for human cell cultivation, horse albumin is used for horse cell cultivation, pig albumin is used for pig cell cultivation, and so on). Unlike presently known species-matched, albumin-supplemented cell culture media which have been used to cultivate hematopoietic cells, the cell culture media according to the present invention have proven effective in cultivating several types of non-hematopoietic animal cells.

Despite the potential problems associated with serum-supplemented cell culture media discussed above, animal serum remains a preferred cell culture supplement for research applications because it is plentiful and comparatively inexpensive. Consequently, the present invention contemplates the use of species-matched serum as an optional supplement in research-grade cell culture media formulations. In contrast, clinical or therapeutic uses of cells cultivated in serum face considerable risks of inducing adverse reactions or other harm to a human or other animal subject in which they are introduced. Accordingly, the clinical-grade cell culture media formulations contemplated herein do not include serum of any kind, whether species-matched or xenogeneic.

As noted above, serum may contain viruses. However, purified albumin derived from serum does not. Concentrated albumin solutions have been long used as a "plasma extender" given to people who have lost large volumes of blood to increase the fluid volume. Because of this application, FDA-approved methods currently exist for essentially "pasteurizing" albumin solutions to inactivate viruses that cannot be removed by filtration. Additionally, purified serum-derived albumin does not contain the antibodies that are present in serum, and it is not immunogenic (i.e., it does not induce development of antibodies in different individuals of a given species). Note, however, that BUMINATE 25% Albumin (HUMAN) Solution (Baxter Healthcare Corporation, Westlake Village, Calif.) is not suitable as supplied for use in the instant invention without additional processing.

Purified albumin is also not sensitive to blood type. That is, albumin derived from a first blood type can be used as a cell culture medium supplement to cultivate cells for use with a recipient of another blood type. Moreover, efficient methods for the purification of albumin have existed for many years and are well known in the art. It can be made from plasma or serum pooled from any blood type.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings wherein.

DETAILED DESCRIPTION OF THE INVENTION

Figure 1:
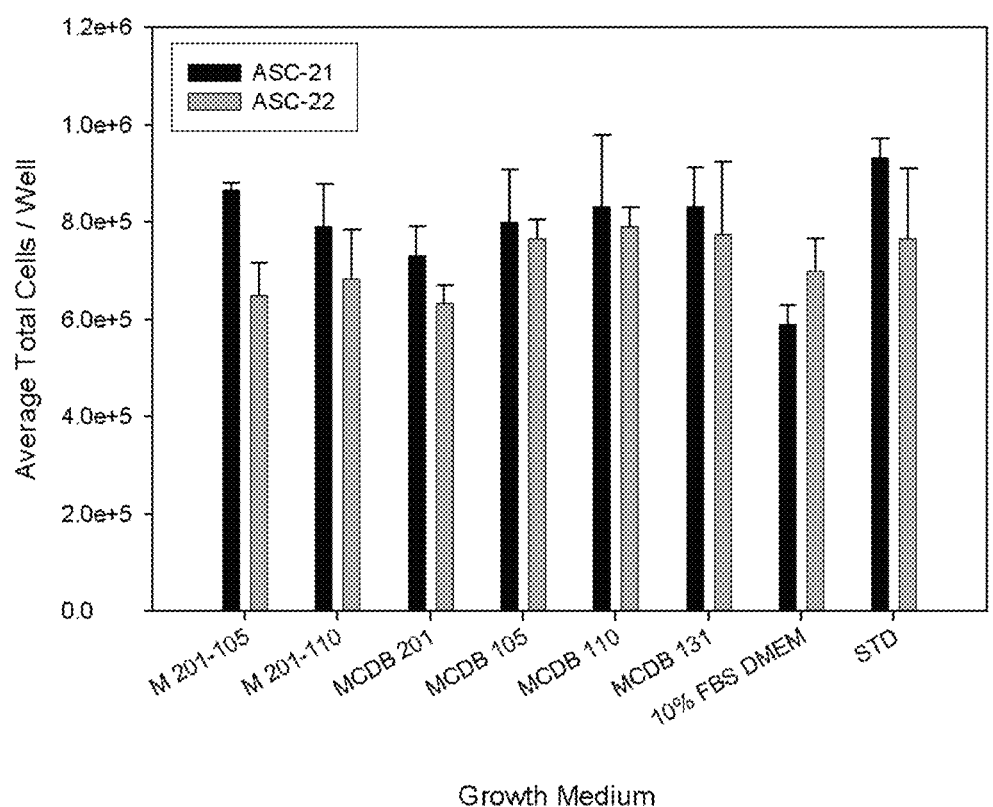
FIG. 1 is a first bar chart graphically representing cell growth performance data of animal cell lines cultivated in cell culture media formulated according to the present invention.

As discussed below, the cell culture media of the present invention has demonstrated efficacy in cultivating primary culture of normal non-hematopoietic mesenchymal stem cells, adipose stromal cells and other mesodermal tissue-derived stem and progenitor cells for both human and non-human animal research and clinical applications. Indeed, the present cell culture media has promoted effective cultivation of adipogenic, chondrogenic, and osteogenic cells. The media may be used to support, without limitation, the cultivation of adipose stromal, subcutaneous stromal, omental stromal, visceral stromal, bone marrow stromal, umbilical cord stromal or placental stromal cell cultures cultivated for human or veterinary clinical purposes and cell cultures cultivated for in vitro research purposes. When used for human or veterinary therapeutic clinical use, the cell culture media of the instant invention are serum-free and xenogeneic product-free to promote the development of low-risk cell cultures and engineered tissues. When used for human or veterinary research applications, the cell culture media of the instant invention are xenogeneic product-free but may be supplemented with species-matched serum or plasma to promote the development of low-risk cell cultures and engineered tissues. Whether intended for clinical or research cell growth, the cell culture media comprise a basal culture media supplemented with the albumin from the species of cells to be cultivated. Significantly, the cell culture media of the present invention have shown effectiveness in cultivating primary cell lines which are typically more difficult to cultivate in the absence of serum than established, continuous (immortalized) cell lines. Continuous cell lines are established by passaging primary cultures. While most human cell cultures have finite lifespans in culture, continuous lines can arise by either the "spontaneous" acquisition of chromosomal abnormalities, or by the introduction of oncogenes. In either event, one is essentially selecting for the cells that grow best under the conditions used (Temin, H. M., Pierson, R. W., and Dulak, N. C., 1972) as opposed to optimizing the conditions for the growth of the initial cell population.

TABLE 1 is a representative but non-limitative cell culture media formulation according to the present invention. Referring to TABLE 1, Culture Medium I (CM-I) is low glucose Dulbecco's Modified Eagle Medium DMEM•LG, Catalog No. 10567-014, marketed by Invitrogen Corporation of Carlsbad, Calif. ("Invitrogen"); Culture Medium II (CM-II) is MCDB 201, Catalog No. M 6770, marketed by Sigma-Aldrich company of St. Louis, Mo. ("Sigma"); and Culture Medium III (CM-III) is MCDB 131, Catalog No. M 8537, also marketed by Sigma. Culture Medium IV is a presently preferred culture medium composition according to the invention, without protein supplements, which is useful un culturing research-grade adipose stromal cells (ASC) and mesenchymal stem cells (MSC). Culture Medium IV is formulated as a 60:20:20 mixture, by volume, of Culture Media I, II and III, respectively. The asterisked (*) values in the instant formulation, Culture Medium IV (CM-IV), indicate constituent concentrations that are substantially different (≥2-fold less than or ≥2-fold greater than) in respect to two or more of the corresponding constituent concentrations of Culture Media I, II and III (underlined) of which Culture Medium IV is composed, and serve to demonstrate the unique composition of the culture medium of the instant invention.

TABLE 1

| MEDIUM: | CM-I (g/l) | CM-II (g/l) | CM-III (g/l) | CM-IV (g/l) |
|---|---|---|---|---|
| COMPONENT | | | | |
| INORGANIC SALTS | | | | |
| NH4VO3 | 0 | 0.000000006 | 0.0000006 | 0.0000001212* |
| CaCl2•2H2O | 0.264 | 0.294 | 0.2352 | 0.26424 |
| CuSO4•5H2O | 0 | 0.00000025 | 0.0000012 | 0.00000029* |
| FeSO4•7H2O | 0 | 0.001668 | 0.000278 | 0.0003892* |
| Fe(NO3)3•9H2O | 0.0001 | 0 | 0 | 0.00006* |
| MgSO4 (anhyd) | 0 | 0.18057 | 1.204 | 0.276914* |
| MgSO4•7H2O | 0.200 | 0 | 0 | 0.12* |
| MnSO4 | 0 | 0.000000075 | 0.0000002 | 0.000000055* |
| (NH4)2MO4•4H2O | 0 | 0.000000618 | 0.0000037 | 0.0000008636* |
| NiCl2•6H2O | 0 | 0.0000000012 | 0.0000001 | 0.00000002024* |
| KCl | 0.400 | 0 | 0.2982 | 0.29964 |
| NaCl | 6.4 | 7.597 | 6.4284 | 6.64508 |
| NaSiO3•9H2O | 0 | 0.000142 | 0.002842 | 0.0005968* |
| Na2HPO4 (anhyd) | 0 | 0.07099 | 0.071 | 0.028398* |
| NaH2PO4•2H2O | 0.141 | 0 | 0 | 0.0846* |
| Na2SeO3 | 0 | 0.000000865 | 0.0000052 | 0.000001213* |
| ZnSO4•7H2O | 0 | 0.000028744 | 0.0000003 | 0.0000058088* |
| AMINO ACIDS | | | | |
| L-Alanine | 0 | 0.00891 | 0.00267 | 0.002316* |
| L-Alanyl-Glutamine | 0.862 | 0 | 0 | 0.5172* |
| L-Arginine•HCl | 0.084 | 0.0632 | 0.06321 | 0.075682 |
| L-Asparagine•H2O | 0 | 0.150 | 0.01501 | 0.033002* |
| L-Aspartic Acid | 0 | 0.01331 | 0.01331 | 0.005324* |
| L-Cysteine•HCl•H2O | 0 | 0.03513 | 0.03512 | 0.01405* |
| L-Cystine | 0.048 | 0 | 0 | 0.0288 |
| L-Glutamic Acid | 0 | 0.01471 | 0.004413 | 0.0038246* |
| L-Glutamine | 0 | 0.14615 | 1.461 | 0.32143* |
| Glycine | 0.030 | 0.00751 | 0.00225 | 0.019952* |
| L-Histidine•HCl•H2O | 0.042 | 0.02097 | 0.04192 | 0.037778 |
| L-Isoleucine | 0.105 | 0.01312 | 0.0656 | 0.078744 |
| L-Leucine | 0.105 | 0.03935 | 0.1312 | 0.09711 |
| L-Lysine•HCl | 0.146 | 0.03654 | 0.1826 | 0.131428 |
| L-Methionine | 0.030 | 0.00448 | 0.01492 | 0.02188 |
| L-Phenylalanine | 0.060 | 0.00496 | 0.03304 | 0.0436 |
| L-Proline | 0 | 0.00576 | 0.01151 | 0.003454* |
| L-Serine | 0.042 | 0.03153 | 0.03153 | 0.037812 |
| L-Threonine | 0.095 | 0.03574 | 0.01191 | 0.06653 |
| L-Tryptophan | 0.016 | 0.00613 | 0.00408 | 0.011642 |
| L-Tyrosine•2Na•2H2O | 0 | 0.01135 | 0.02252 | 0.006774 |
| L-Tyrosine | 0.072 | 0 | 0 | 0.0432 |
| L-Valine | 0.094 | 0.03513 | 0.1171 | 0.086846 |
| VITAMINS | | | | |
| Biotin | 0 | 0.00000733 | 0.0000073 | 0.000002926* |
| Choline Chloride | 0.0040 | 0.01396 | 0.01396 | 0.007984 |
| Folic Acid | 0.0040 | 0 | 0 | 0.0024* |
| Folinic Acid•Ca | 0 | 0.00000512 | 0.0005115 | 0.000103324* |
| myo-Inositol | 0 | 0.01802 | 0.007208 | 0.0050456* |
| i-Inositol | 0.0072 | 0 | 0 | 0.00432* |
| Niacinamide | 0.0040 | 0.00611 | 0.006105 | 0.004843 |
| Pantothenic Acid•1/2 Ca | 0 | 0.000477 | 0.011915 | 0.0024784* |
| Pyridoxine•HCl | 0.0040 | 0.0000617 | 0.002056 | 0.00282354 |
| Riboflavin | 0.00040 | 0.000113 | 0.0000038 | 0.00026336* |
| Thiamine•HCl | 0.0040 | 0.000337 | 0.003373 | 0.003142 |
| Vitamin B-12 | 0 | 0.000136 | 0.0000136 | 0.00002992* |
| OTHER | | | | |
| Adenine•HCl | 0.00172 | 0.00172 | 0.0001716 | 0.00141032 |
| Ethanolamine | 0 | 0 | 0 | 0.002* |
| Glucose | 1.0 | 1.441 | 1.0 | 1.0882 |
| HEPES | 0 | 7.149 | 0 | 1.4298* |
| Linoleic Acid | 0 | 0.0000841 | 0 | 0.00001682* |
| Phenol Red•Na | 0.015 | 0.001242 | 0.0124212 | 0.01173264 |

TABLE 1-continued

| MEDIUM: | CM-I (g/l) | CM-II (g/l) | CM-III (g/l) | CM-IV (g/l) |
|---|---|---|---|---|
| Putrescine•2HCl | 0 | 0.000000161 | 0.0000002 | 0.000000072* |
| Pyruvic Acid•Na | 0.11 | 0.055 | 0.11 | 0.099 |
| Thioctic Acid | 0 | 0.00000206 | 0.0000021 | 0.000000832* |
| Thymidine | 0 | 0.0000727 | 0.0000242 | 0.00001938* |
| NaHCO3 | 3.7 | 0 | 1.18 | 2.456 |
| Powder (g) to prepare 1 liter | 0 (liquid) | 17.7 | 11.7 | 15.3 |

Tables 2 and 3, respectively, are representative but non-limitative, formulations according to the present invention (including growth factor additives) for a research-grade adipose stromal cell (ASC) establishment and growth medium and a research-grade medium for establishment and growth of mesenchymal stem cells (MSC) from bone marrow, umbilical cord blood or the placenta.

TABLE 2

| 0.5% FBS ASC Medium | per 250 ml |
|---|---|
| 0.5% Fetal bovine serum (FBS) | 1.25 ml |
| 1X ITS-X (Invitrogen #51500-056) | 2.5 ml 100X stock |
| 0.2% Bovine serum albumin (BSA) | 25.0 ml 2% stock |
| 1X Linoleic Acid-BSA (Sigma #L9530) | 2.5 ml 100X stock |
| 100 µM L-Ascorbate-2-phosphate | 2.5 ml 10 mM stock |
| 100 µM β-mercaptoethanol | 0.45 ml 55 mM stock |
| 10 ng/ml rhEGF | 0.25 ml 10 µg/ml stock |
| 5 ng/ml rhPDGF-BB | 125 µl 10 µg/µl stock |
| 1 nM dexamethasone | 25 µl 10 µM stock |
| in DMEM: MCDB 201: MCDB 131 (60:20:20): | 215.4 ml: |
| DMEM (low glucose) | 129.24 ml |
| MCDB 201 | 43.1 ml |
| MCDB 131 | 43.0 ml |

TABLE 3

| 2% FBS MSC Medium | per 250 ml |
|---|---|
| 2.0% FBS | 5.0 ml |
| 1X ITS-X (Invitrogen #51500-056) | 2.5 ml 100X stock |
| 0.2% Bovine serum albumin (BSA) | 12.5 ml 2% stock |
| 1X Linoleic Acid-BSA (Sigma #L9530) | 2.5 ml 100X stock |
| 100 µM L-Ascorbate-2-phosphate | 2.5 ml 10 mM stock |
| 100 µM β-mercaptoethanol | 0.45 ml 55 mM stock |
| 10 ng/ml rhEGF | 0.25 ml 10 µg/ml stock |
| 5 ng/ml rhPDGF-BB | 125 µl 10 ng/µl stock |
| 1 nM dexamethasone | 25 µl 10 µM stock |
| in DMEM: MCDB 201: MCDB 131 (60:20:20): | |
| DMEM (low glucose) | 137.75 ml |
| MCDB 201 | 43.1 ml |
| MCDB 131 | 43.1 ml |

Tables 4 and 5, respectively, are representative but non-limitative formulations according to the present invention (including growth factor additives) for establishment and growth of clinical-grade adipose stromal cells for human use and establishment and growth of clinical-grade adipose stromal cells for veterinary use.

TABLE 4

| Human ASC Medium | per 250 ml |
|---|---|
| rhInsulin | 2.5 ml 100X stock |
| rhTransferrin* | 2.5 ml 100X stock |
| 4% Human serum albumin (HSA) | 50 ml 20% stock |
| 1X Linoleic Acid-HSA | 2.5 ml 100X stock |
| 100 µM L-Ascorbate-2-phosphate | 2.5 ml 10 mM stock |
| 100 µM β-mercaptoethanol | 0.45 ml 55 mM stock |
| 10 ng/ml rhEGF | 0.25 ml 10 µg/ml stock |
| 5 ng/ml rhPDGF-BB | 125 µl 10 µg/µl stock |
| 1 nM dexamethasone | 25 µl 10 µM stock |
| 0.000007913 g sodium selenite | 2.5 ml 0.00067 g/l stock |
| in DMEM: MCDB 201: MCDB 131 (60:20:20): | 189.2 ml |
| DMEM (low glucose) | 113.6 ml |
| MCDB 201 | 37.8 ml |
| MCDB 131 | 37.8 ml |

* Or Transferrin from human plasma

TABLE 5

| Animal ASC Medium | per 250 ml |
|---|---|
| Insulin* | 2.5 ml 100X stock |
| Transferrin§ | 2.5 ml 100X stock |
| 4% Albumin† | 50 ml 20% stock |
| 1X Linoleic Acid-HSA | 2.5 ml 100X stock |
| 100 µM L-Ascorbate-2-phosphate | 2.5 ml 10 mM stock |
| 100 µM β-mercaptoethanol | 0.45 ml 55 mM stock |
| 10 ng/ml rhEGF | 0.25 ml 10 µg/ml stock |
| 5 ng/ml rhPDGF-BB | 125 µl 10 µg/µl stock |
| 1 nM dexamethasone | 25 µl 10 µM stock |
| 0.000007913 g sodium selenite | 2.5 ml 0.00067 g/l stock |
| in DMEM: MCDB 201: MCDB 131 (60:20:20): | 189.2 ml |
| DMEM (low glucose) | 113.6 ml |
| MCDB 201 | 37.8 ml |
| MCDB 131 | 37.8 ml |

*From bovine or porcine pancreas.
§From bovine plasma or serum.
†From plasma or serum of bovine, equine, porcine or other animal species of interest.

Table 6 contains representative but non-limitative, generally clinical-grade, non-hematopoietic, adipose stromal cell differentiation media formulations according to the present invention.

TABLE 6

| Adipogenic Differentiation Medium |
|---|
| (ADM; 25 ml) in DMEM:HF12 (1:1) plus 1% HSA§ |
| 33 µM biotin (0.25 ml "100x" 3.3 mM stock) |
| 0.1 µM dexamethasone (0.25 ml of 10 µM freshly diluted in DMEM:HF12 from 5 mM stock)* |
| 1 µM Insulin (50 µl "1000x" 500 µM stock)‡ |
| 200 µM indomethacin (50 µl of 200 mM stock in DMSO) |
| 17 µM pantothenic acid (25 µl "1000x" 17 mM stock) |
| 0.2 nM triiodothyronine (25 µl "1000x", freshly diluted from $10^6 \times 0.2$ mM stock) |

TABLE 6-continued

10 µg/ml transferrin (25µl of 10 mg/ml stock)‡
§ Or substitute albumin from the appropriate species for
animal cells. For Adipogenic Induction Medium (AIM), add
250 µM 3-isobutyl-1-methylxanthine (IBMX) (25 µl of 250 mM
stock) OR 125 µM IBMX (12.5 µl stock) + 2.2 µM Troglitazone
(25 µl stock) OR 4.4 µM Troglitazone (50 µl stock)
*0.1-1 µM; higher conc. only with serum present (1% calf
or horse serum)
‡ Or replace Insulin and Transferrin with ITS-X (0.25 ml of
100X stock in research grade applications)
Chondrogenic Differentiation Medium (CDM; 25 ml) in DMEM plus 1% HAS
100 nM L-Ascorbic acid 2-phosphate (25 µl of 100X dilution
from 10 mM stock)
1 µM Insulin (50 µl "1000x" 500 µM stock)
10 ng/ml recombinant TGF-β1 (25 µl of 10 µg/ml stock)
Myogenic Differentiation Medium (MDM; 25 ml) in DMEM plus 1% HAS
0.1 µM dexamethasone (0.25 ml of 10 µM freshly diluted in
DMEM:HF12 from 5 mM stock)
50 µM hydrocortisone
Osteogenic Differentiation Medium (ODM; 25 ml) in DMEM plus 1% HAS
100 µM L-Ascorbic acid 2-phosphate (0.25 ml of 10 mM stock)
10 mM (β-glycerophosphate (0.25 ml of 1 M stock)
0.1 µM dexamethasone (0.25 ml of 10 µM freshly diluted in
DMEM:HF12 from 5 mM stock)*
[5 mM sodium phosphate (0.25 ml of 500 mM Na$_2$HPO$_4$:NaH$_2$PO$_4$
(~5:1), pH 7.4)]**
*Or 0.2 µM hydrocortisone **Added after 7-14 days
Neuronal Differentiation Medium (NDM; 25 ml) in DMEM plus 4% HAS
100 µM (β-mercaptoethanol (25 µl of 100 mM stock)
1 µM all trans-retinoic acid (250 µl of 0.1 mM stock in
Ethanol:DMEM:HF12 (2:1:1), freshly diluted from 10 mM DMSO
stock, then filter sterilized)
1X B27 (0.25 ml of 100X stock supplement)
[200 µM BHA (25 µl of 200 mM stock)]*
[2% DMSO (0.25 ml of 20% DMSO in DMEM)]*

*Optional

Table 7 is a qualitative representation of the cell differentiation capability of thirteen different human adipose stromal cell strains that were established and grown in cell culture media formulated in accordance with the present invention. More particularly, human adipose stromal cell strains were established and grown in 0.5% FBS ASC medium and were tested for adipogenic, chondrogenic, and osteogenic differentiation capability by either PrimeCell Therapeutics LLC, a subsidiary of PrimeGen Biotech LLC, both of Irvine, Calif.[A], the Coriell Institute for Medical Research of Camden, N.J.[B], or both[C]. For each category, positive differentiation is indicated by (+), and negative differentiation is indicated by (−). All cells lines, except for ASC-25[1], showed 50% or greater adipogenic differentiation. Osteogenic and chondrogenic differentiation was confirmed in all of the ASC lines, except for ASC-5, however the degree to which was not determined. In three of the ASC lines, the cells plated in chondrogenic differentiation medium spontaneously aggregated to form spheroid bodies[2].

TABLE 7

| Cell Line | Adipogenesis | Chondrogenesis | Osteogenesis |
|---|---|---|---|
| ASC-5[A] | + | + | − |
| ASC-7[A] | + | + | + |
| ASC-11[A] | + | + | + |
| ASC-12[A] | + | + | + |
| ASC-13[A] | + | + | + |
| ASC-16[C] | + | +[2] | + |
| ASC-17[A] | + | + | + |
| ASC-20[A] | + | + | + |
| ASC-25[B] | +[1] | +[2] | + |
| ASC-26[B] | + | + | + |
| ASC-27[B] | + | + | + |
| ASC-23[A] | + | + | + |
| ASC-32[B] | + | +[2] | + |

Turning to the figures, FIG. 1 is a comparison of the growth response of ASC-21 and ASC-22 cells to different basal media. Cells were plated in a standard ASC medium (0.5% FBS ASC), on human fibronectin (hFN) coated 6-well plates and cultured in the following media: M 201:105 (1:1), M 201:110 (1:1), MCDB 201, MCDB 105, MCDB 110, MCDB 131, 10% FBS:DMEM, and ASC Culture Medium CM-IV of TABLE 1, which contains DMEM•LG:MCDB 201:MCDB 131 (60:20:20). All media, except 10% FBS:DMEM, were supplemented with the same mixture and concentration of growth factors as the standard ASC medium. Data plotted represent the mean counts+/−standard deviations of triplicate wells counted after 3 days of growth. Culture Medium CM-IV of TABLE 1 produced the most ASC-21 cell growth and produced growth in ASC-22 cells similar to that of MCDB 105, 110, and 131.

Figure 2:
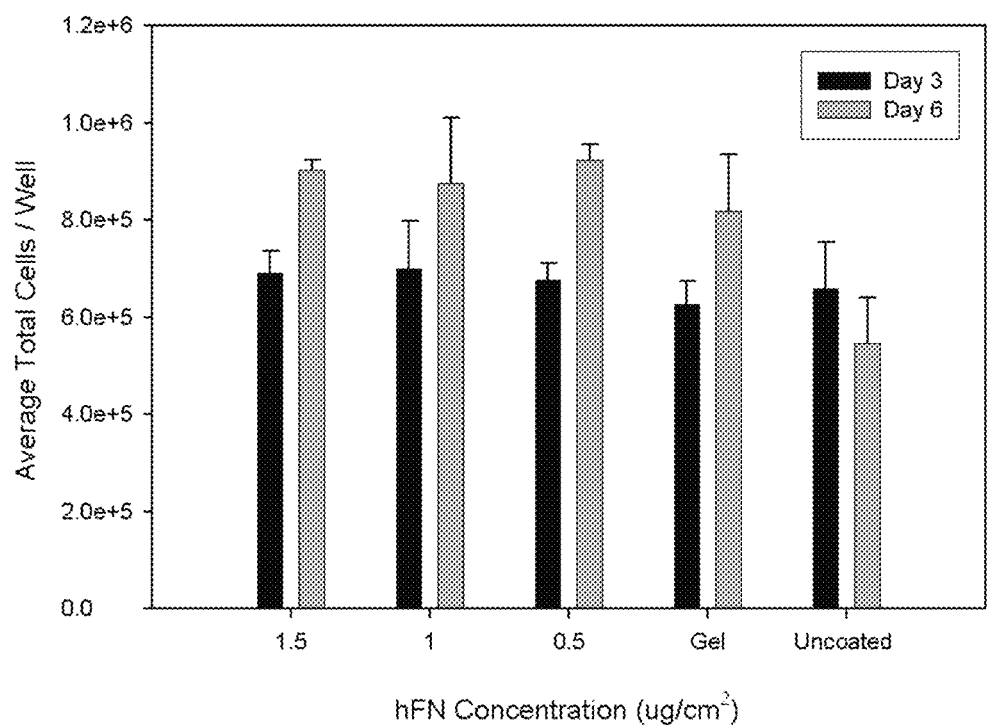
FIG. 2 is a further bar chart graphically representing cell growth performance data of animal cell lines cultivated in cell culture media formulated according to the present invention.

FIG. 2 is a comparison of ASC-28 cell growth on six well plates coated with either 1.5, 1.0, and 0.5 µg/cm$^2$ human fibronectin (hFN), gelatin, or left uncoated. Cells were plated in duplicate conditions and cultured in a standard ASC medium (0.5% FBS ASC). Data plotted represent the mean counts+/−standard deviations of duplicate wells. While the growth stimulation by hFN at Day 3 was slight, at Day 6 all concentrations of hFN and gelatin coated wells produced significantly better cell growth than the uncoated wells. However, only human fibronectin is suitable for clinical applications.

Figure 3:
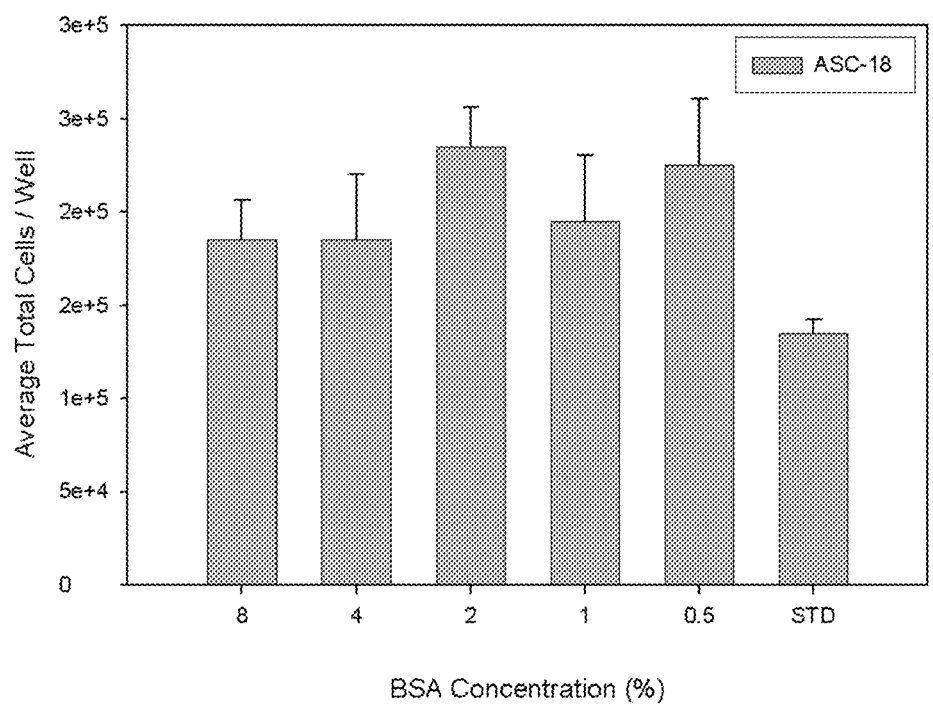
FIG. 3 is a further bar chart graphically representing cell growth performance data of animal cell lines cultivated in cell culture media formulated according to the present invention.

FIG. 3 is a comparison of the growth response of ASC-18 cells to 0.5, 1, 2, 4, and 8% Bovine Serum Albumin (BSA) ASC medium, using Sigma A-4503 BSA. The cells were initially plated in a standard ASC medium (0.5% FBS ASC), switched to the indicated media after one day (day 0), and counted after more days of growth. Data plotted represent the mean counts+/−standard deviations of duplicate wells. All BSA concentrations of A-4503 produced a better growth response than the standard ASC medium. Of all the BSA concentrations, 0.5% was the optimal concentration for cell growth, based on the growth response to the minimal level of protein.

Figure 4:
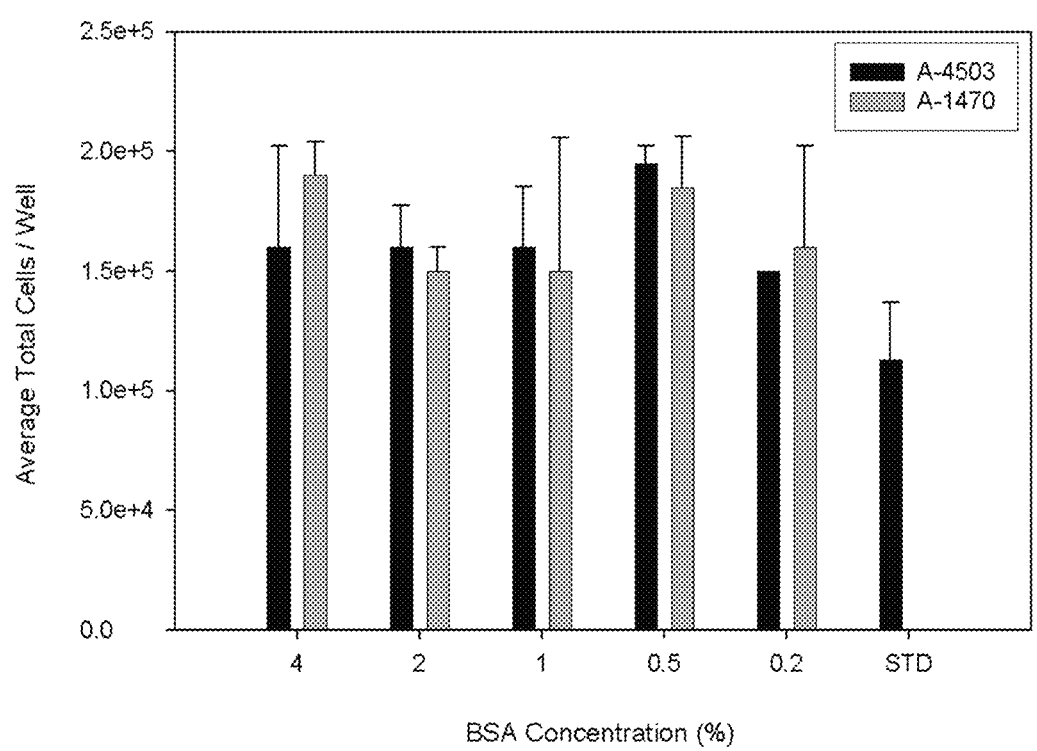
FIG. 4 is a further bar chart graphically representing cell growth performance data of animal cell lines cultivated in cell culture media formulated according to the present invention.

FIG. 4 is a comparison of the growth response of ASC-19 cells to 0.2, 0.5, 1, 2, and 4% Bovine Serum Albumin (BSA) ASC medium, using either Sigma A-4503 or A-1470 BSA. The cells were initially plated in a standard ASC medium (0.5% FBS ASC), switched, in duplicate or triplicate (1% and 2%), to the test media the next day (day 0), and counted after 3 more days of growth. Data plotted represent the mean counts+/−standard deviations of duplicate (1% BSA) or triplicate (2% BSA) wells. All concentrations of A-4503 and A-1470 produced a better growth response than the standard ASC medium. Of all the BSA concentrations, including A-4503 and A-1470, 0.5% A-4503 produced the most cell growth, with less variation than that obtained with A-1470.

Figure 5:
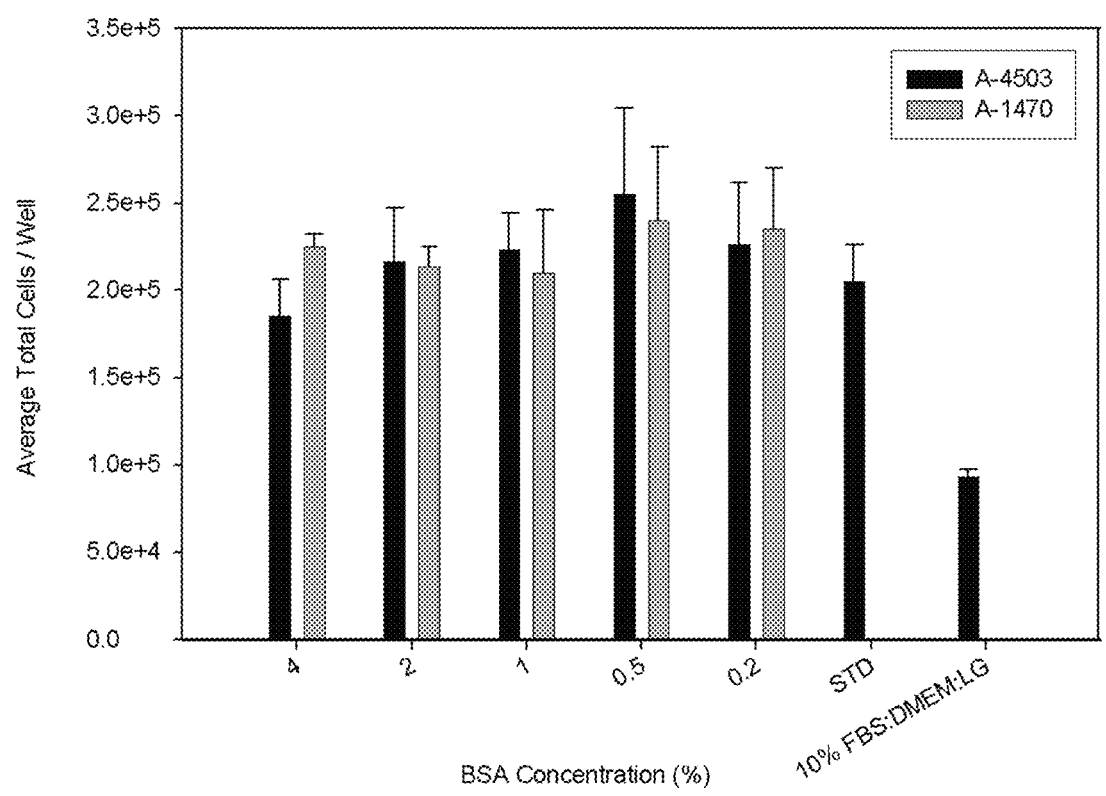
FIG. 5 is a further bar chart graphically representing cell growth performance data of animal cell lines cultivated in cell culture media formulated according to the present invention.

FIG. 5 is a comparison of the growth response of ASC-19 cells to 0.2, 0.5, 1, 2, and 4% Bovine Serum Albumin (BSA) ASC medium, using either Sigma A-4503 or A-1470 BSA. The cells were initially cultured in a standard ASC medium (0.5% FBS ASC), switched to the test media on day 0, fed again with the respective media on day 3, and counted on day 6. Data plotted represent the mean counts+/−standard deviations of duplicate (1% BSA) or triplicate (2% BSA) wells. All concentrations of A-4503 and A-1470 produced much better growth than 10% FBS:DMEM. Of all the BSA concentrations, 0.5% A-4503 produced the most cell growth.

Figure 6:
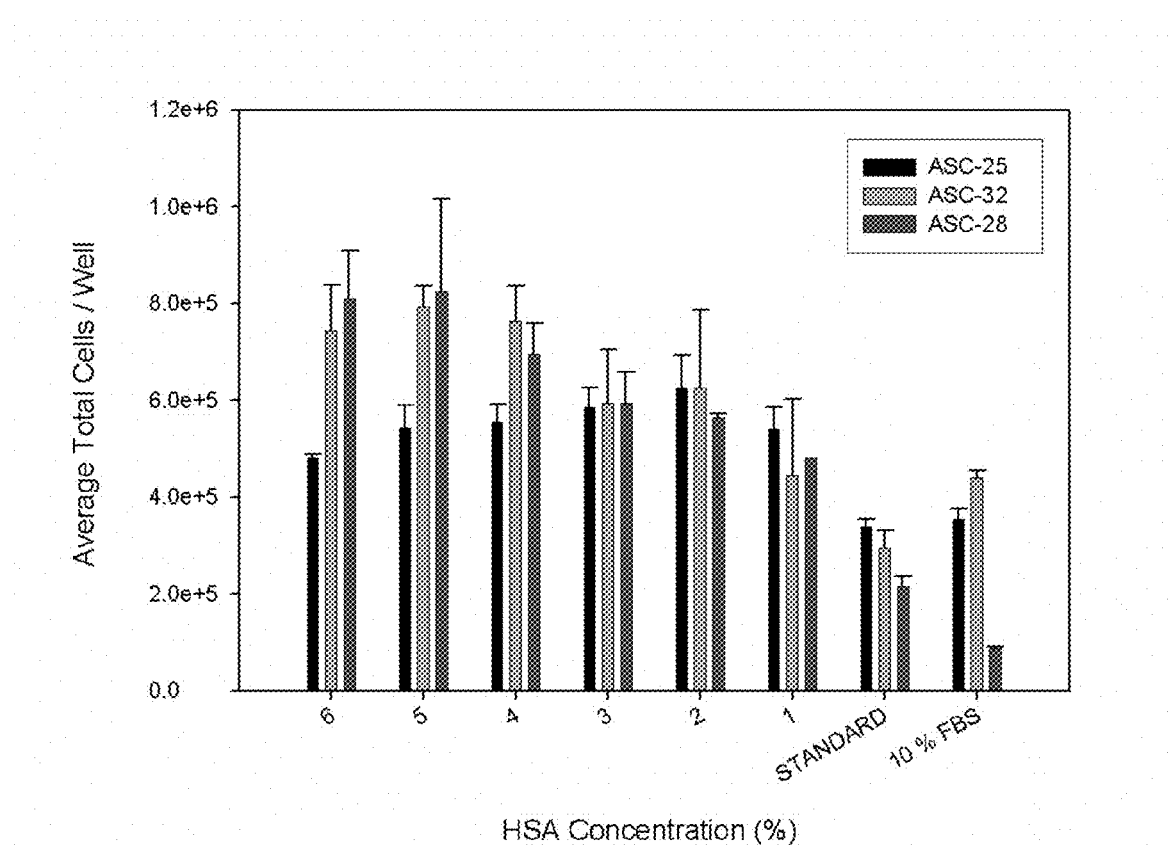
FIG. 6 is a further bar chart graphically representing cell growth performance data of animal cell lines cultivated in cell culture media formulated according to the present invention.

FIG. 6 is a comparison of the growth responses of ASC-25, 32, and 28 cells to 1, 2, 4, 5, and 6% Human Serum Albumin (HSA) ASC medium, using Sigma A-1653 HSA. The cells were plated in a standard ASC medium (0.5% FBS ASC), switched to the respective growth media on day 0, and counted on day 3. Data plotted represent the mean counts+/−standard deviations of duplicate (ASC-28) or triplicate (ASC-25 and 32) wells. All three ASC cell lines showed a better growth response, at each HSA concentration, than the standard ASC medium and all three lines produced a better growth response at the optimal HSA concentration than 10% FBS:DMEM.

Figure 7:
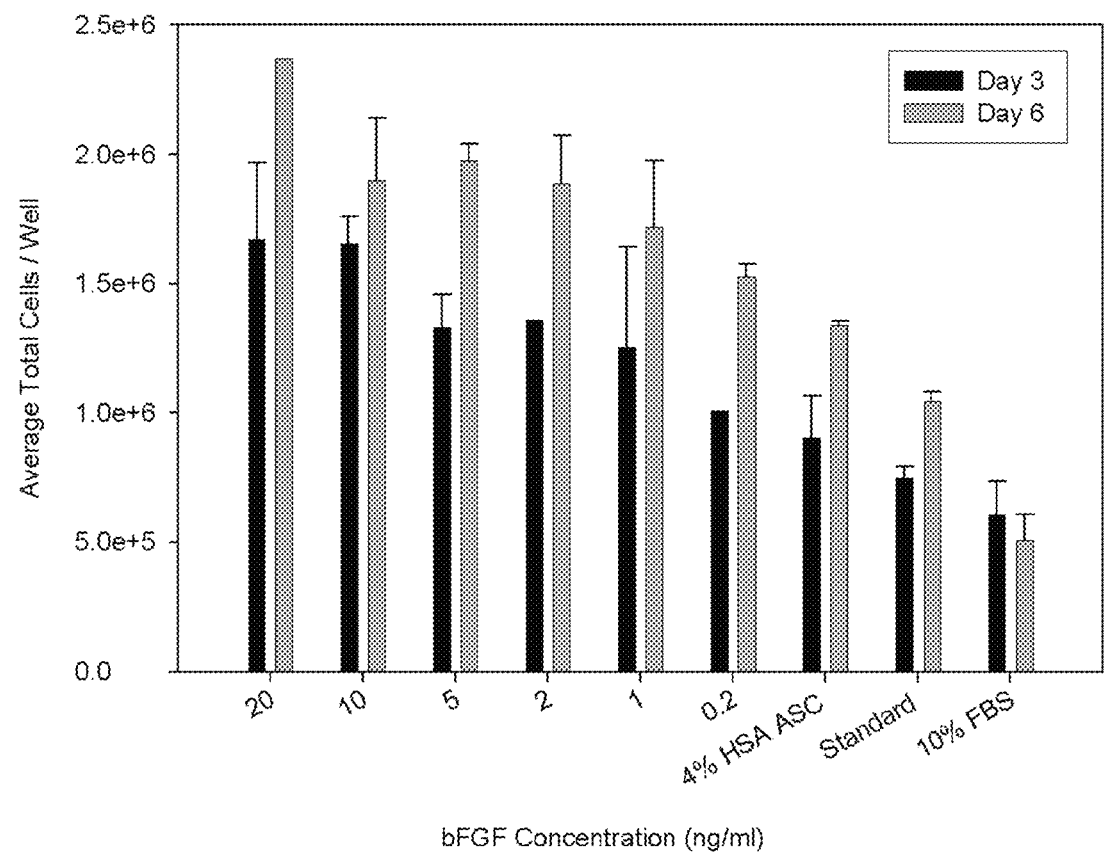
FIG. 7 is a further bar chart graphically representing cell growth performance data of animal cell lines cultivated in cell culture media formulated according to the present invention.

FIG. 7 is a comparison of the growth response at Day 3 and 6 of ASC-20 cells to 0.2, 1, 2, 5, 10, and 20 ng/ml bFGF in 4% Human Serum Albumin (HSA), using Sigma A-1653 HAS, to cells cultured without bFGF in a standard ASC medium (0.5% FBS ASC), 4% HSA ASC medium, and 10% FBS:DMEM (low glucose). The cells were plated in the standard ASC medium, switched to the indicated test media on day 0. Duplicate wells were counted on day 3, and the remaining wells were fed with the respective media on day 3 and counted on day 6. Data plotted represent the mean counts+/−standard deviations of duplicate wells. All concentrations of bFGF produced a better growth response, with cell growth increasing with bFGF concentration, than the three control media.

Figure 8:
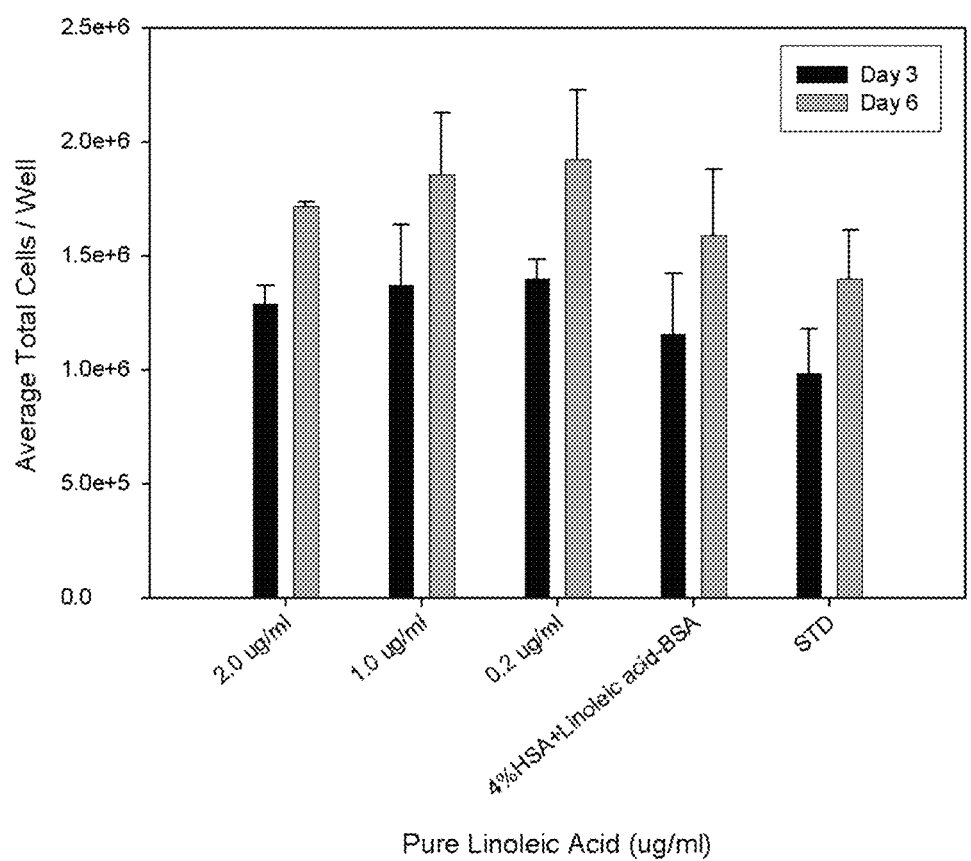
FIG. 8 is a further bar chart graphically representing cell growth performance data of animal cell lines cultivated in cell culture media formulated according to the present invention.

FIG. 8 is a comparison of the growth response at Day 3 and 6 of ASC-28 cells to either 2.0, 1.0, or 0.2 μg/ml of pure Linoleic Acid in 4% Human Serum Albumin (HSA) ASC medium, using Sigma A-1653 HSA, to cells cultured in a standard ASC medium (0.5% FBS ASC) and 4% HSA ASC medium containing 0.01682 μg/ml Linoleic acid in the basal medium plus 4.22 μg/ml (0.1%) of Linoleic Acid-BSA. The cells were plated in the standard ASC medium and switched to the indicated media on day 0. Triplicate wells were counted on day 3, and the remaining wells were fed with the respective media on day 3 and counted on day 6. Data plotted represent the mean counts+/−standard deviations of triplicate wells. All three concentrations of pure Linoleic Acid in 4% HSA ASC produced a better growth response than Linoleic Acid-BSA in 4% HSA ASC and the standard medium.

The following is a discussion of possible additions to or variations of cell culture media according to the present invention which may find beneficial application either alone or in combination depending on the species and type of cells to be cultivated.

In many formulations the supplement may include at least one of growth factors, hormones and cytokines. For example, and as set forth in greater detail below, the supplement may include one or more of dexamethasone, epidermal growth factor (EGF), basic fibroblast growth factor (bFGF or FGF-2), platelet-derived growth factor-BB (PDGF-BB), insulin, transferrin, linoleic acid, beta-mercaptoethanol (2-mercaptoethanol), sodium selenite, and L-ascorbate 2-phosphate.

As noted above, the albumin supplement is species-matched to the species of cells to be cultivated. If human source albumin is used to support cultivation of human cells, the human source albumin may be human plasma- or serum-derived albumin or recombinant human albumin in concentrations of between about 0.5 and 10 grams (g) per 100 milliliters (ml). In a preferred embodiment, the human albumin concentration is about 4 g/100 ml. The recombinant human albumin may be recombinant protein derived from the human albumin gene expressed in a prokaryotic or eukaryotic microbe.

The supplement may also include recombinant human epidermal growth factor (rhEGF) in concentrations of between about 2 and 50 nanograms (ng) per ml. In a preferred embodiment, the rhEGF concentration is about 10 ng/ml.

The supplement may further comprise recombinant human platelet-derived growth factor-BB (rhPDGF-BB) in concentrations of between about 2 and 20 ng/ml. In a preferred embodiment, the rhPDGF-BB concentration is about 5 ng/ml.

The supplement may also include recombinant human basic fibroblast growth factor (bFGF) in concentrations of between about 0.1 to 100 ng/ml. In a preferred embodiment, the bFGF concentration is about 10 ng/ml.

The supplement may further include insulin-like growth factor 1 (IGF-1) in concentrations of between about 0.1 to 100 ng/ml. In a preferred embodiment, the concentration of IGF-1 is about 10 ng/ml.

The supplement may further include at least one of endothelin-1 (ET-1), endothelin-2 (El-2) and endothelin-3 (ET-3) in concentrations of between about 0.01 to 100 ng/ml. In a preferred embodiment, the concentration of endothelin is about 10 ng/ml.

The supplement may further comprise recombinant human hepatocyte growth factor (HGF) in concentrations of between about 0.1 ng/ml to 100 ng/ml. In a preferred embodiment, the concentration of HGF is about 2 ng/ml.

If non-human source albumin is used to support cultivation of non-human animal cells, the animal source albumin may be of avian (chicken), bovine (cow), canine (dog), caprine (goat), equine (horse), feline (cat), murine (mouse), ovine (sheep), porcine (pig) or rat origin. If bovine, the animal source albumin may be bovine plasma- or serum-derived albumin or recombinant bovine albumin in concentrations of between 0.1 and 4 g/100 ml (i.e., 0.1% and 4%). In a preferred embodiment, the bovine albumin concentration is about 0.5 g/100 ml. Alternatively, the animal source albumin may be fetuin (the fetal form of albumin) or recombinant fetuin that replaces bovine plasma- or serum-derived albumin in concentrations of between about 0.1 and 4 g/100 ml (i.e., 0.1% and 4%). In a preferred embodiment, the fetuin concentration is about 0.5 g/100 ml. For veterinary applications, the supplement may comprises plasma- or serum-derived equine (horse), canine (dog), caprine (goat), avian (chicken), feline (cat), ovine (sheep), porcine (pig) or rat albumin, or recombinant versions thereof, replacing bovine albumin in concentrations of between about 0.1 and 4 g/100 ml (i.e., 0.1% and 4%). In a preferred embodiment, the animal albumin concentration is about 0.5 g/100 ml.

The supplement may also include insulin (INS). The insulin may be present in concentrations of between about 1 and 50 milligrams (mg) per liter (l). In a preferred embodiment, the insulin concentration is about 10 mg/l. The insulin may be a recombinant protein produced in a microorganism. For non-human animal applications, the insulin may be of avian (chicken), bovine (cow), canine (dog), caprine (goat), equine (horse), feline (cat), murine (mouse), ovine (sheep), porcine (pig) or rat origin.

The supplement may also include transferrin (TF). The transferrin may be present in concentrations of between about 1 and 50 mg/l. In a preferred embodiment, the transferrin concentration is about 5.5 mg/l. The transferrin may be a recombinant protein produced in a microorganism. For non-human animal applications, the transferrin may be of avian (chicken), bovine (cow), canine (dog), caprine (goat), equine (horse), feline (cat), murine (mouse), ovine (sheep), porcine (pig) or rat origin.

The supplement may additionally comprise 2-mercaptoethanol in concentrations of between about 50 and 500 micromolar (μM). In a preferred embodiment, the 2-mercaptoethanol concentration is about 100 μM.

The supplement may also comprise L-ascorbic acid 2-phosphate in concentrations of between about 50 and 500 μM. In a preferred embodiment, the L-ascorbic acid 2-phosphate concentration is about 100 μM.

The supplement may additionally include dexamethasone in concentrations of between 0.1 and 100 nanomolar (nM). In a preferred embodiment, the dexamethasone concentration is about 1 nM.

Additionally, the supplement may include phenol red or the sodium salt thereof, as well as HEPES buffer.

When cultivating an animal cell culture using the culture media of the present invention, the animal cell culture is brought into contact with the media on a culture vessel or substrate under conditions suitable to support cultivation of the animal cell culture. Such conditions may include first coating a culture vessel or substrate with adhesion-promoting substrata. The adhesion-promoting substrata may comprise human fibronectin or functional fibronectin fragment, with or without collagen. The fibronectin or functional fibronectin fragment substrate may be derived from human plasma, or, for veterinary applications, from the plasma of the species of interest. In the alternative, the human fibronectin or functional fibronectin fragment may be a recombinant protein derived from the human fibronectin gene or a fragment thereof, or, for veterinary applications, from the gene of the species of interest expressed in a prokaryotic or eukaryotic microbe. The fibronectin or functional fibronectin fragment may be added to the culture substrate at 0.5 to 20 micrograms (μg) per square centimeter (cm$^2$) of surface area. In a preferred embodiment, the fibronectin is added at 1.5 μg/cm$^2$.

A preferred method of cultivating an animal cell culture according to the invention further includes using non-enzymatic neutral-buffered dissociation solutions containing at least one of ethylene glycol-bis(2-aminoethylether)-N,N,N', N-tetraacetic acid (EGTA) or ethylene diamine tetraacetic acid (EDTA) and sodium salts thereof to remove cells from a culture substrate. In a preferred embodiment, the cells are washed once with calcium- and magnesium-free phosphate-buffered saline (PBS), and removed from the substrate by incubation in calcium- and magnesium-free phosphate-buffered saline containing 0.01 and 1 g/100 ml (i.e., 0.01% to 1%) EGTA or EDTA, or sodium salts thereof. In a preferred embodiment, the EGTA or EDTA concentration is about 0.1 g/100 ml. An alternative dissociation solution is non-animal derived trypsin produced in a microorganism such as recombinant trypsin or similar proteolytic enzyme (e.g., TrypLE marketed by Invitrogen.

The cell culture media described herein may be used alone or as part of a kit including any one of the foregoing dissociation solutions or other suitable dissociation solution. When using such a kit, proteolytic enzyme resulting from use of the kit is preferably neutralized and the dissociated cells are re-suspended in calcium- and magnesium-free phosphate-buffered saline (PBS) or similar neutral, isotonic buffer containing from about 0.01 and 1 g/100 ml (i.e., 0.01% to 1%) soybean trypsin inhibitor. In a preferred embodiment, the trypsin inhibitor concentration is about 0.05 g/100 ml.

Although the invention has been described in detail for the purpose of illustration, it is to be understood that such detail is solely for that purpose and that variations can be made therein by those skilled in the art without departing from the spirit and scope of the invention as claimed herein.

What is claimed is:

1. A cell culture medium for clinical growth of adipose stromal cells from a species to be cultivated for clinical and therapeutic applications, said medium comprising:
   (a) a basal medium suitable for mammalian cell culture and human albumin for clinical growth of human adipose stromal cells for human clinical and therapeutic applications from the species to be cultivated;
   (b) at least one of (i) growth promoting amounts of insulin from the species to be cultivated, (ii) transferrin from the species to be cultivated, (iii) recombinant epidermal growth factor from the species to be cultivated at a concentration of about 10.0 ng/ml, (iv) recombinant platelet-derived growth factor-BB from the species to be cultivated at a concentration of about 5.0 ng/ml, and (v) human recombinant basic fibroblast growth factor;
   (c) L-ascorbate-2-phosphate solution in a concentration of 100 μM;
   (d) 2-mercaptoethanol in a concentration of 100 μM;
   (e) dexamethasone solution in a concentration of 1 nM; and
   (f) phenol red.

* * * * *